US007463919B2

(12) United States Patent
Hamilton et al.

(10) Patent No.: US 7,463,919 B2
(45) Date of Patent: Dec. 9, 2008

(54) CARDIAC DIAGNOSTICS USING WALL MOTION AND PERFUSION CARDIAC MRI IMAGING AND SYSTEMS FOR CARDIAC DIAGNOSTICS

(75) Inventors: Craig A. Hamilton, Lewisville, NC (US); William Gregory Hundley, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 932 days.

(21) Appl. No.: 10/628,915

(22) Filed: Jul. 29, 2003

(65) Prior Publication Data
US 2004/0073105 A1 Apr. 15, 2004

Related U.S. Application Data

(60) Provisional application No. 60/421,708, filed on Oct. 28, 2002, provisional application No. 60/399,275, filed on Jul. 29, 2002.

(51) Int. Cl.
*A61B 5/05* (2006.01)
(52) U.S. Cl. ........................... 600/410; 324/154
(58) Field of Classification Search ............ 600/427, 600/410, 431, 413; 128/653.1; 345/619; 324/309; 382/154
See application file for complete search history.

(56) References Cited

U.S. PATENT DOCUMENTS

| 5,111,820 | A |   | 5/1992 | Axel et al. | 128/653 |
|---|---|---|---|---|---|
| 5,431,161 | A | * | 7/1995 | Ryals et al. | 600/425 |
| 5,908,386 | A | * | 6/1999 | Ugurbil et al. | 600/410 |
| 6,292,683 | B1 | * | 9/2001 | Gupta et al. | 600/410 |
| 6,434,412 | B1 | * | 8/2002 | Simonetti et al. | 600/410 |
| 6,597,940 | B2 | * | 7/2003 | Bishop et al. | 600/436 |
| 6,892,089 | B1 | * | 5/2005 | Prince et al. | 600/410 |
| 6,894,707 | B2 |   | 5/2005 | Nemoto | 345/730 |
| 7,047,060 | B1 | * | 5/2006 | Wu | 600/410 |
| 2003/0018251 | A1 | * | 1/2003 | Solomon | 600/427 |
| 2003/0120151 | A1 | * | 6/2003 | Constantinides | 600/431 |
| 2004/0027359 | A1 | * | 2/2004 | Aharon et al. | 345/619 |
| 2004/0057607 | A1 | * | 3/2004 | Breeuwer et al. | 382/128 |

FOREIGN PATENT DOCUMENTS

WO    WO 00/43800    *    7/2000

OTHER PUBLICATIONS

Declaration of Dr. Craig Hamilton Pursuant to 37 C.F.R. 1.131, 8 sheets, executed Jun. 6, 2007.
International Search Report dated Jan. 23, 2004 for corresponding PCT application No. PCT/US03/23526.

(Continued)

*Primary Examiner*—Eric F Winakur
*Assistant Examiner*—Lawrence N Laryea
(74) *Attorney, Agent, or Firm*—Myers, Bigel, Sibley & Sajovec, P.A.

(57) ABSTRACT

Cardiac information of a patient is displayed by obtaining a plurality of MRI cine loops of the heart of the patient at a plurality of heart rates, the plurality of cine loops including both wall motion cine loops and at least one perfusion cine loops and simultaneously displaying both the wall motion cine loops and the at least one perfusion cine loop.

25 Claims, 6 Drawing Sheets

OTHER PUBLICATIONS

Bellenger et al. "Reduction in Sample Size for Studies of Remodeling in Heart Failure by the Use of Cardiovascular Magnetic Resonance" *J Cardiovascular Mangn Reson* 2(4): 271-278 (2000) (Abstract).

Bristow et al. "Doxorubicin Cardiomyopathy: Evaluation by Phonocardiography, Endomyocardial Biopsy, and Cardiac Catheterization" *Annals of Internal Medicine* 88: 168-175 (1978).

Cerqueira et al. "Standardized Myocardial Segmentation and Nomenclature for Tomographic Imaging of the Heart: A Statement for Healthcare Professionals from the Cardiac Imaging Committee of the Council on Clinical Cardiology of the American Heart Association" *Circulation* 150: 539-542 (2002).

Choi et al. "Transmural Extent of Acute Myocardial Infarction Predicts Long-Term Improvement in Contractile Function" *Circulation* 104: 1101-1107 (2001).

Chuang et al. "Importance of Imaging Method Over Imaging Modality in Noninvasive Determination of Left Ventricular Volumes and Ejection Fraction: Assessment by Two- and Three-Dimensional Echocardiology and Magnetic Resonance Imaging" *Journal of the American College of Cardiology* 35(2): 477-484 (2000).

Darty et al. "Nursing Responsibilities During Cardiac Magnetic Resonance Imaging" Department of Internal Medicine (Cardiology Section) and Radiology at the Wake Forest University School of Medicine (no date).

Del Carlo et al. "Cardiac Troponins in Congestive Heart Failure" *American Heart Journal* 138: 646-653 (1999).

Gerber et al. "Relation Between Gd-DTPA Contrast Enhancement and Regional Inotropic Response in The Periphery and Center of Myocardial Infarction" *Circulation* 104:998-1004 (2001).

Gianni et al. "Cardiac Function Following Combination Therapy with Taxol (T) and Doxorubicin (A) for Advanced Breast Cancer (ABC)" *Proceedings of ASCO* vol. 17 (1998) (Abstract).

Gottdiener et al. "Doxorubicin Cardiotoxicity: Assessment of Late Left Ventricular Dysfunction by Radionuclide Cineangiography" *Annals of Internal Medicine* 94(part 1): 430-435 (1981).

Hamilton et al. "Is Imaging at Intermediate Doses Necessary During Dobutamine Stress Magnetic Resonance Imaging?" *Journal of Cardiovascular Magnetic Resonance* 3(4): 297-302 (2001).

Hundley et al. "Relation of Cardiac Prognosis to Segment Location with Apical Left Ventricular Ischemia" *The American Journal of Cardiology* 92: 1206-1208 (2003).

Hundley et al. "Utility of Fast Cine Magnetic Resonance Imaging an display for the Detection of Myocardial Ischemia in patients Not Well Suited for Second Harmonic Stress Echocardiography" *Circulation* 100: 1697-1702 (1999).

Jacobson et al. "Magnetic Resonance Imaging of the Cardiovascular System: Present State of the Art and Future Potential" *JAMA* 259(2): 253-259 (1988).

Jensen et al. "Functional Monitoring of Anthracycline Cardiotoxicity: A Prospective, Blinded, Long-Term Observational Study of Outcome in 120 Patients" *Annals of Oncology* 13: 699-709 (2002).

Judd et al. "Physiological basis of Myocardial Contrast Enhancement in Fast Magnetic Resonance Images of 2-Day-Old Reperfused Canine Infarcts" *Circulation* 92: 1902-1910 (1995).

Kellman et al. "Phase-Sensitive Inversion Recover for Detecting Myocardial Infarction Using Gadolinium-Delayed Hyperenhancement" *Magnetic Resonance in Medicine* 47: 372-383 (2002).

Kim et al. "The Use of Contract-Enhanced Magnetic Resonance Imaging to Identify Reversible Myocardial Dysfunction" *New England Journal of Medicine* 343: 1445-1453 (2000).

Longmore et al. "Dimensional Accuracy of Magnetic Resonance in Studies of the Heart" *The Lancet* pp. 1360-1362 (Jun. 15, 1985).

Lorenz et al. "Normal Human Right and Left Ventricular Mass, Systolic Function, and Gender Differences by Cine Magnetic Resonance Imaging" *J Cardiovascular Magn Reson* 1(1): 7-21 (1999).

Maisel et al. "B-Type Natriuretic Peptide Levels: Diagnostic and Prognostic in Congestive Heart Failure: What's Next?" *Circulation* 150: 2328-2331 (2002).

Martin et al. "Imaging Cardiac Structure and Pump Function" *Cardiac Magnetic Resonance Imaging* 16(2): 135-160 (1998).

McDonagh et al. "Biochemical Detection of Left-Ventricular Systolic Dysfunction" *The Lancet* 351: 9-13 (1998).

Pattynama et al. "Left Ventricular Measurements with Cine and Spin-Echo MR Imaging: A Study of Reproducibility with Variance Component Analysis" *Radiology* 187: 261-268 (1993).

Rector et al. "Assessment of Patient Outcome with the Minnesota Living Heart Failure Questionnaire: Reliability and Validity During Randomized, Double-Blind, Placebo-Controlled Trial of Pimobendan" *Amercian Heart Journal* 124: 1017-1025 (1992).

Rehr et al. "Left Ventricular Volumes Measured by MR Imaging" *Radiology* 156: 717-719 (1985).

Rerkpattanapipat et al. "Clinical Utility of Assessments of Left Ventricular Systolic Function and Coronary Arterial Blood Flow During Pharmacological Stress with Magnetic Resonance Imaging" *Topics in Magnetic Resonance Imaging* 11(6): 399-405 (2000).

Schwartz et al. "Congestive Heart Failure and Left Ventricular Dysfunction Complicating Doxorubicin Therapy" *The American Journal of Medicine* 82: 1109-1109-1118 (1987).

Sechetem et al. "Measurement of Right and Left Ventricular Volumes in healthy Individuals with cine MR Imaging" *Radiology* 163: 697-702 (1987).

Semelka et al. "Interstudy Reproducibility of Dimensional and Functional Measurements Between Cine Magnetic Resonance Studies in the Morphologically Abnormal Left Ventricle" *American Heart Journal* 119: 1367-1373 (1990).

Stratemeier et al. "Ejection Fraction Determination by MR Imaging: Comparison with Left Ventricular Angiography" *Radiology* 158: 775-777 (1986).

Wu et al. "Visualisation of Presence, Location, and Transmural Extent of Healed Q-Wave and Non-Q-Wave Myocardial Infarction" *The Lancet* 357: 21-28 (2001).

Rule 132 Declaration of Craig A. Hamilton of Pre-Patent Filing Activity, 2 sheets, executed Feb. 8, 2007.

A patient consent form referenced in Document 1, 3 sheets (earlier than Jul. 29, 2001).

Hundley et al. "Utility of Fast Cine Magnetic Resonance Imaging an display for the Detection of Myocardial Ischemia in patients Not Well Suited for Second Harmonic Stress Echocardiography" *Circulation* 100: 1697-1702 (1999). (Article referenced in Document 1).

Hamilton et al. "Is Imaging at Intermediate Doses Necessary During Dobutamine Stress Magnetic Resonance Imaging?" *Journal of Cardiovascular Magnetic Resonance* 3(4): 297-302 (2001). (Article referenced in Document 1).

* cited by examiner

CARDIAC DIAGNOSTICS USING WALL MOTION AND PERFUSION CARDIAC MRI IMAGING AND SYSTEMS FOR CARDIAC DIAGNOSTICS

RELATED APPLICATIONS

This application claims the benefit of priority of U.S. Provisional Patent Application Ser. No. 60/399,275, filed Jul. 29, 2002, and U.S. Provisional Patent Application Ser. No. 60/421,708 filed Oct. 28, 2002, the contents of which are hereby incorporated by reference as if recited in full herein.

FIELD OF THE INVENTION

The present invention is related to cardiac diagnostics and more particularly to stress test cardiac diagnostics using magnetic resonance imaging (MRI) methods.

BACKGROUND OF THE INVENTION

The heart is a muscle that continuously pumps blood, transporting life sustaining oxygen and nutrients to the major organs and tissues of the body. As such, the heart needs a large supply of oxygen and nutrients. The heart receives its blood from three major coronary arteries. If any one of these arteries becomes narrowed or blocked, blood flow and oxygen to the heart is restricted, the performance of your blood pump is impaired, and permanent damage to the heart can occur. An impaired or damaged heart can significantly impact quality of life and even result in death.

Coronary artery disease (CAD) is the primary cause of narrowing and blockage of the arteries to or in the heart. It is the leading cause of death in the United States. Although the rate of death due to CAD has declined steadily over the last few decades, the overall incidence of CAD and the impact it will have on the population and the cost of health care is expected to grow dramatically over the next 20-30 years due to the aging population. CAD already costs the U.S. an estimated $100 billion annually in medical care and lost productivity. Therefore, the tests for CAD that can improve the accuracy of cardiac evaluations, particularly in early stage coronary heart disease/CAD, may be beneficial. Tests that may allow physicians to make explicit diagnoses and treatment plans, that may reduce unnecessary tests, surgeries and hospital stays, may reduce anxiety, discomfort and risk to the patient and/or may allow for the assessment of therapeutic efficacy may be particularly beneficial.

The ability to mitigate and circumvent the effects of CAD has improved over the years as a result of the prior development of increasingly sophisticated cardiac tests and procedures. The "gold standard" of cardiac tests is generally recognized as cardiac catheterization and angiography. This test is most commonly used in determining the location and the severity of the effects of CAD. However, a cardiac catheterization procedure is an expensive procedure that typically requires hospitalization because it is invasive and has potential for complications. As a result, cardiac catheterization procedures are generally only used when a patient has undergone other non-invasive tests such as cardiac stress tests with significant abnormal results. More than one million cardiac catheterization procedures are performed each year at a cost estimated to be between about $3-$5 billion.

Cardiac stress tests may be particularly important in evaluating the heart and its coronary arteries because often the presence of CAD and its effects are missed when tests are performed on a patient at rest. It is only when the heart is stressed by either exercise on a treadmill or exercise bike, or where the maximal exercise is simulated by the introduction of special chemicals or drugs (drug-induced stress) to the heart of patients who for various reasons are unable to perform actual physical exercise, that the symptoms of CAD can be reliably detected over much of the population. Currently, the most commonly used stress tests include the exercise (treadmill) stress test, the stress echocardiogram (ultrasound), and the nuclear perfusion stress test.

These three tests have varying levels of complexity, accuracy, availability, and cost. The ECG exercise stress test is the most widely available and used stress test and the least costly to administer. It relies on detection of changes in ST segments on a 12-lead echocardiogram; it is variable in its accuracy, producing a significant number of false positive and negative results. Consequently, patients often undergo supplemental imaging during their stress test with echocardiography or radionuclide scintigraphy. The sophistication of both echocardiography and radionuclide scintigraphy stress tests typically require that they be administered and evaluated by a specialist. Typically, a trained ultrasound technician or a cardiologist administers a stress echocardiogram, and a technician certified in the handling of radioisotopes along with a cardiologist or radiologist administers a nuclear perfusion stress test. Results in both testing protocols generally need to be evaluated by a cardiologist in order to make an accurate diagnosis. The test selected for administration is typically determined by the cardiologist based on the findings of the physical and medical history of the patient and the cardiologist's clinical judgment. Each test has a degree of inaccuracy. The echocardiography has an almost 10-15% failure rate where a diagnosis cannot be made. Obstacles that may prevent the capture of good images for diagnosis may cause this failure rate. Scar tissue from chest surgeries, excessive patient body fat and lung disorders that capture excessive oxygen in the lungs are examples of such obstacles. Stress echocardiography tests, for varying reasons, also produce a significant number of false negative results. The nuclear perfusion stress tests are highly sensitive and are prone to produce an equally significant number of false positive results.

With over 1.3 million stress echocardiography tests performed each year with a 10-15% failure rate, there are potentially over $100 million unnecessary or clinically unreliable stress echocardiography tests done each year. This stress echo failure rate results in an increase in the number of nuclear perfusion stress tests, which are known to have a high incidence of false positive results. A false positive cardiac stress test may increase the number of expensive, unnecessary cardiac catheterization procedures and their associated required hospital stay and added anxiety, discomfort and medical risk for the patient. The significant number of false negatives from stress echocardiography tests may increase the risk of heart attacks and sudden death from undetected advanced CAD and/or successful earlier intervention in early stages of CAD.

Accordingly, a need exists for reduced cost, increased accuracy and/or increased availability stress testing for cardiac diagnostics.

SUMMARY OF THE INVENTION

Embodiments of the present invention provide methods, system and/or computer program products for displaying cardiac information of a patient. A plurality of MRI cine loops of the heart of the patient are obtained at a plurality of heart rates and levels of pharmacologic and/or exercise induced stress. The plurality of cine loops including wall motion cine loops of frames of wall motion images and perfusion images of at lease one cardiac location. Both the wall motion cine loops and the perfusion cine loop are simultaneously displayed.

In certain embodiments, the perfusion image is at least one cine loop of perfusion images of at least one location of the heart. In further embodiments, the perfusion image is a myocardial delayed enhancement (MDE) perfusion image of a location of the heart.

In particular embodiments of the present invention, the plurality of MRI cine loops are adjusted so as to provide compensated cine loops having a same number of frames in each of the MRI cine loops. Furthermore, the plurality of MRI cine loops may be acquired while a stress test is administered to the patient. The displayed MRI cine loops may also be evaluated to determine a presence or absence of myocardial ischemia or viability based on the displayed cine loops.

In further embodiments of the present invention, for a single dosage of a stress inducing agent or level of exercise, a plurality of cine loops for differing locations associated with the heart of the patient are simultaneously displayed. A plurality of cine loops for a single location associated with the heart of the patient for differing dosages of a stress inducing drug may also be simultaneously displayed.

In still other embodiments of the present invention, the plurality of MRI cine loops are adjusted by adding frames to and/or removing frames from at least one of the plurality of MRI cine loops. Frames may be added to and/or removed from respective ones of the MRI cine loops such that all of the displayed MRI cine loops have a same number of frames. Furthermore, the additional frames may be provided by repeating frames of an MRI cine loop. The frames that are added or removed may be evenly distributed throughout an MRI cine loop.

In additional embodiments of the present invention, the wall motion MRI cine loops are compensated such that corresponding frames in each of the plurality of wall motion MRI cine loops correspond to a common portion within a cardiac cycle of the patient. Thus, frames in different cine loop may correspond to a different duration of time, time, however, each frame may correspond to the same percentage of time of the cardiac cycle.

Furthermore, the plurality of MRI cine loops may also be adjusted by adjusting a duration of display of frames of a least one of the plurality of MRI cine loops such that each of the MRI cine loops has a common total duration. In additional embodiments of the present invention, cardiac information of a patient is displayed by obtaining a plurality of MRI cine loops of the heart of the patient at a plurality of heart rates, the plurality of cine loops including cine loops including frames of wall motion images. At least one perfusion image of at least one cardiac location is also obtained. Both the wall motion cine loops and the at least one perfusion image are simultaneously displayed.

In certain embodiments of the present invention, the perfusion image is a plurality of perfusion images that provide a cine loop of perfusion images. In such a case, simultaneously displaying both wall motion cine loops and the at least one perfusion image is provided by simultaneously displaying both wall motion cine loops and the at least one cine loop of perfusion images.

In other embodiments of the present invention, the perfusion image is a myocardial delayed enhancement perfusion image.

In still further embodiments of the present invention, a user interface for MRI imaging evaluation is provided. The user interface may be displayed on a display device and includes at least one region configured to display a plurality of cine loops of MRI images of cardiac wall motion and at least one region configured to display at least one MRI image of cardiac perfusion. The region configured to display at least one MRI image of cardiac perfusion may be configured to display at least one cine loop of MRI images of cardiac perfusion. Furthermore, the plurality of cine loops of MRI images of cardiac wall motion may be synchronized to one another and the at least one cine loop of MRI images of cardiac perfusion. Also, at least one of the plurality of cine loops of MRI images of cardiac wall motion may be registered to the cine loop of MRI images of cardiac perfusion.

As will be appreciated by those of skill in the art in light of the present disclosure, embodiments of the present invention may be provided as methods, system and/or computer program products.

DESCRIPTION OF EMBODIMENTS OF THE INVENTION

Figure 1:
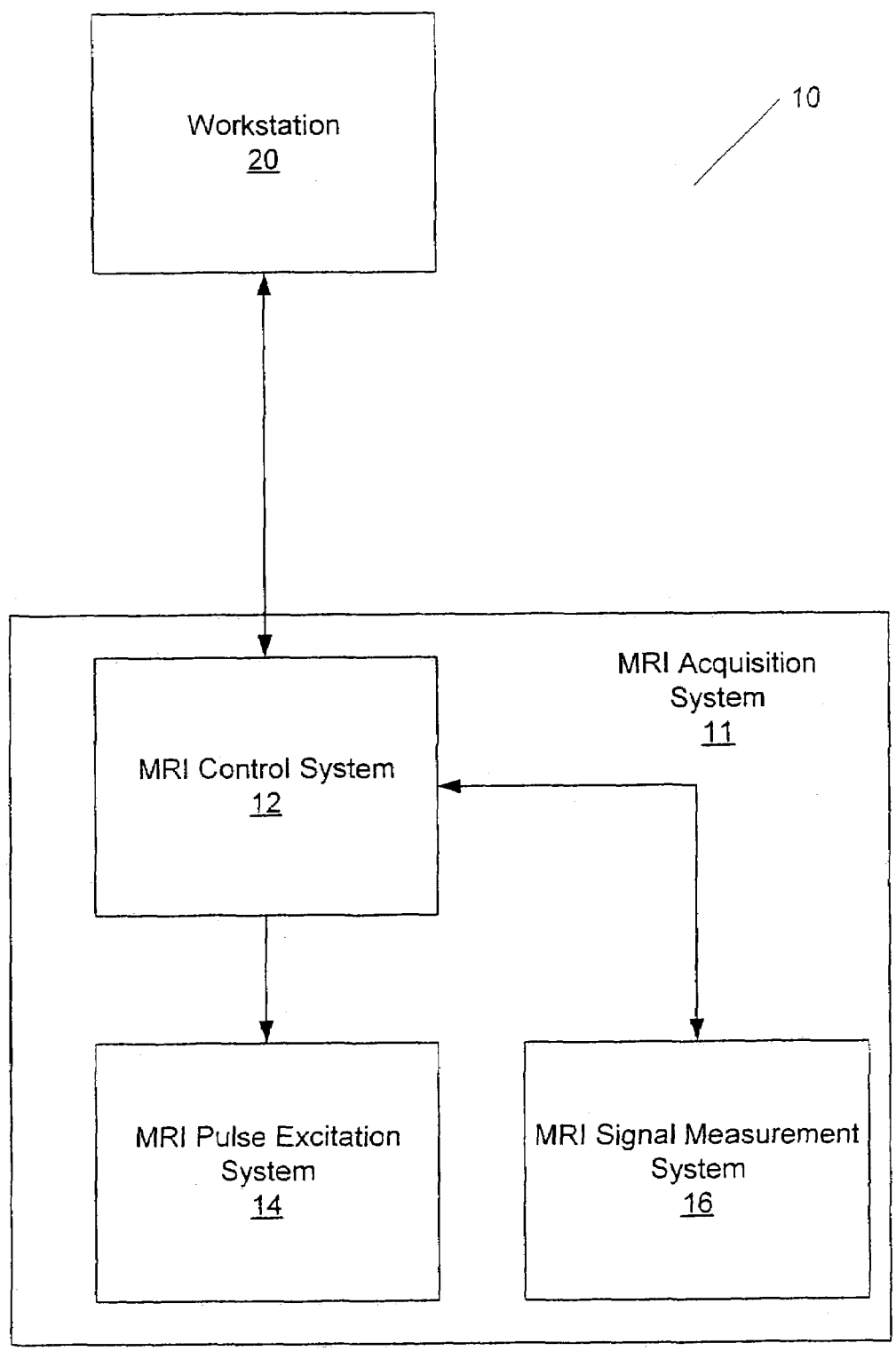
FIG. 1 is a block diagram of an MRI system according to embodiments of the present invention.

The present invention now will be described more fully hereinafter with reference to the accompanying drawings, in which illustrative embodiments of the invention are shown. This invention may, however, should not be construed as limited to the embodiments set forth herein; rather, these embodiments are provided so that this disclosure will be thorough and complete, and will fully convey the scope of the invention to those skilled in the art.

As will be appreciated by one of skill in the art, the present invention may be embodied as methods, systems, or computer program products. Accordingly, the present invention may take the form of an entirely hardware embodiment, an entirely software embodiment or an embodiment combining software and hardware aspects all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. Particular cine display systems may utilize interactive data language (IDL) programming to provide cine displays suitable for use in embodiments of the present invention. The program code may execute entirely on a user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider). Furthermore, the user's computer, the remote computer, or both, may be integrated into other systems, such as an MRI system.

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

Embodiments of the present invention provide for the cardiac diagnostics utilizing both wall motion MRI cine loops of the heartbeat of a patient and perfusion images. The perfusion images may be cine loops of MRI perfusion images and/or individual images, such as may be provide by myocardial delayed enhancement. The wall motion MRI cine loops may be temporally synchronized MRI cine loops adjusted to compensate for different heart rates, such as stress induced heart rates, and, accordingly, different cardiac cycle patterns and/or durations. Cardiac diagnostics are performed by evaluating the temporally synchronized MRI cine loops and one or both of perfusion images or MRI cine loops of a patient being subjected to stress testing. Such evaluation may result in a screening determination as to the likelihood a patient has CAD.

An exemplary system 10 according to embodiments of the present invention is illustrated in FIG. 1. As seen in FIG. 1, a cine display/MRI system 10 includes an MRI acquisition system 11 that may include an MRI control system circuit 12, an MRI pulse excitation system circuit 14 and an MRI signal measurement system circuit 16. The MRI control system circuit 12 controls operations of the MRI acquisition system 11 to obtain and provide MRI images during a cardiac cycle of a patient. The MRI control system circuit 12 may also assemble and transmit the acquired images to a workstation 20 or other such data processing system for further analysis and/or display. The workstation 20 may be in an MRI suite or may be remote from the MRI suite. The MRI pulse excitation system circuit 14 and the MRI signal measurement system circuit 16 are controlled to acquire MRI signals that may provide MRI images of the heart of a patient.

The MRI images may be acquired, for example, utilizing a fast gradient echo segmented k-space sequence. The k-space segmentation may be adjusted to provide adequate temporal resolution (13-65 msec) for identification of end of systole, with the end-systolic frame typically being the frame with the smallest left ventricle (LV) cavity dimensions. View sharing may be utilized to provide an intermediate frame between acquired frames. The table below provides an example of the adjustment of k-space segmentation for differing heart rates.

| Heart Rate (beats/min) | Views per Segment | Temporal Resolution (msec) | Breathhold Duration (sec) |
| --- | --- | --- | --- |
| <55 | 10 | 65 | 10 |
| 55-65 | 8 | 52 | 13-11 |
| 65-95 | 6 | 39 | 15-10 |
| 95-125 | 4 | 26 | 15-12 |
| 125-170 | 2 | 13 | 23-17 |

Alternatively, images may be acquired with other MRI techniques highlighting thickening or relaxation of the LV myocardium.

The MRI images of wall motion and perfusion of the frames of the cine loops may include corresponding images of different locations of the heart and at different times during the cardiac cycle of the patient (i.e. cine loops may be registered to other cine loops). For example, the images may include slices such as the basal short axis, the long axis, the mid short axis, the apical short axis, four chamber and two chamber slices. In particular embodiments, the desired image locations may be selected so as to provide images of LV wall motion. Furthermore, the images may be from different times during a stress test of the patient, for example, at a baseline or resting heart rate and/or at different heart rates and/or different dosages of stress inducing agents, such as dobutamine and atropine.

Myocardial perfusion images will be acquired at rest and during stress (pharmacologic or exercise) upon the administration of paramagnetic contrast agents (such as those containing gadolinium) or susceptibility agents (such as those containing iron oxide or dysprosium), or without the administration of contrast incorporating techniques such as blood-oxygen level dependent (BOLD) cardiac imaging using a T2 prepared pulse sequence or a 3D T2 weighted sequence. The acquired cardiac wall perfusion images may be images of a single location within the cardiac region taken over multiple successive heartbeats. The perfusion images may also be generated and displayed to provide a cine loop having the same number of frames as the corresponding temporally compensated MRI cine loops of wall motion.

Conventional MRI systems, such as those provided by General Electric Medical Systems, Siemens, Philips, Varian, Bruker, Marconi and Toshiba may be utilized to provide the desired MRI image frames collected during heartbeats of a patient undergoing stress testing that may be temporally compensated and displayed and/or analyzed for biophysical or biophysiological abnormalities for cardiac diagnostics according to embodiments of the present invention as described herein.

While an exemplary cine display/MRI system is illustrated in FIG. 1 and described herein with a particular division of functions and/or operations, as will be appreciated by those of skill in the art, other divisions of functions and/or operations may be utilized while still benefiting from the teachings of the present invention. For example, the MRI control system circuit 12 could be combined with either the MRI pulse excitation system circuit 14 or the MRI signal measurement system circuit 16. Thus, the present invention should not be construed as limited to a particular architecture or division of MRI functions/operations but is intended to cover any architecture or division of functions/operations capable of carrying out the operations described herein.

Figure 2:
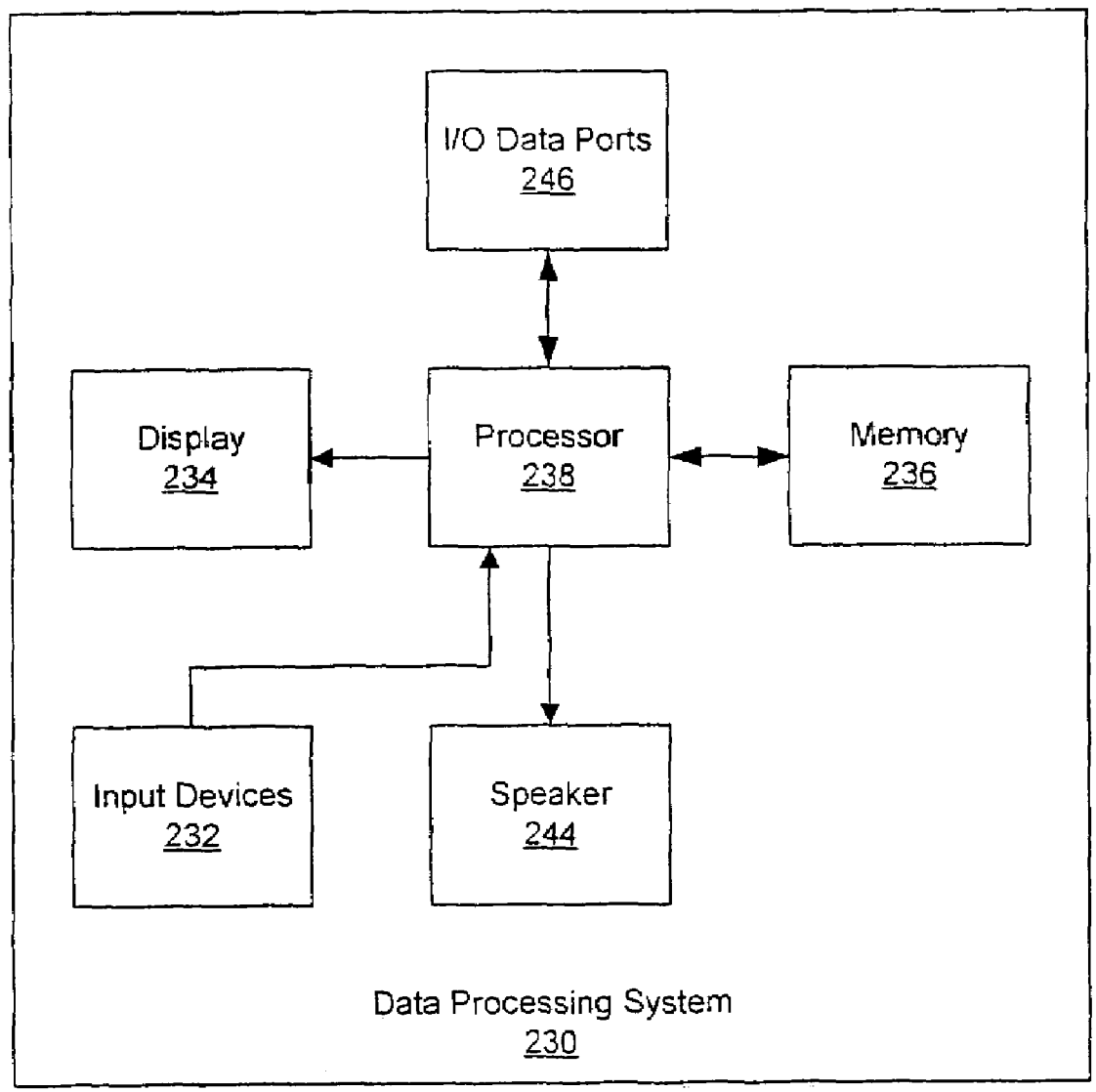
FIG. 2 is a block diagram of a data processing system according to embodiments of the present invention.

FIG. 2 illustrates an exemplary embodiment of a data processing system 230 suitable for providing a workstation 20 and/or MRI control system circuit 12 in accordance with embodiments of the present invention. The data processing system 230 typically includes input device(s) 232 such as a keyboard or keypad, a display 234, and a memory 236 that communicate with a processor 238. The data processing system 230 may further include a speaker 244, and an I/O data port(s) 246 that also communicate with the processor 238. The I/O data ports 246 can be used to transfer information between the data processing system 230 and another computer system or a network. These components may be conventional components such as those used in many conventional data processing systems that may be configured to operate as described herein.

Figure 3:
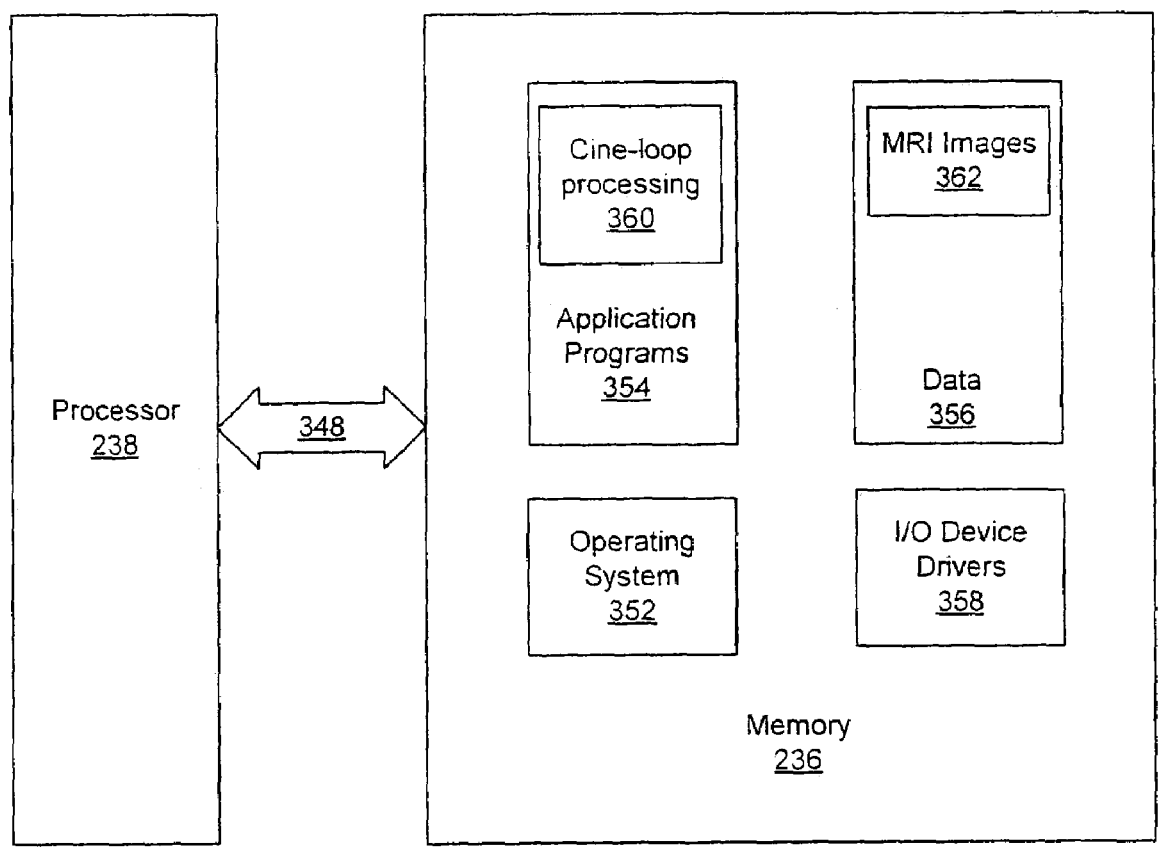
FIG. 3 is a more detailed block diagram of a MRI cine loop display system according to embodiments of the present invention.

FIG. 3 is a block diagram of embodiments of data processing systems that illustrates systems, methods, and computer program products in accordance with embodiments of the present invention. The processor 238 communicates with the memory 236 via an address/data bus 348. The processor 238 can be any commercially available or custom microprocessor. The memory 236 is representative of the overall hierarchy of memory devices containing the software and data used to implement the functionality of the data processing system 230. The memory 236 can include, but is not limited to, the following types of devices: cache, ROM, PROM, EPROM, EEPROM, flash memory, SRAM, and DRAM.

As shown in FIG. 3, the memory 236 may include several categories of software and/or data used in the data processing system 230: the operating system 352; the application programs 354; the input/output (I/O) device drivers 358; and the data 356. As will be appreciated by those of skill in the art, the operating system 352 may be any operating system suitable for use with a data processing system, such as OS/2, AIX or System390 from International Business Machines Corporation, Armonk, N.Y., Windows95, Windows98, Windows2000, WindowsNT or WindowsXP from Microsoft Corporation, Redmond, Wash., Unix or Linux. The operating systems may be configured to support an TCP/IP-based or other such network communication protocol connection. The I/O device drivers 358 typically include software routines accessed through the operating system 352 by the application programs 354 to communicate with devices such as the I/O data port(s) 246 and certain memory 236 components. The application programs 354 are illustrative of the programs that implement the various features of the data processing system 230 and preferably include at least one application that supports operations according to embodiments of the present invention. Finally, the data 356 represents the static and dynamic data used by the application programs 354, the operating system 352, the I/O device drivers 358, and other software programs that may reside in the memory 236.

As is further seen in FIG. 3, the application programs 354 may include a cine-loop processing application 360. The cine-loop processing application 360 may carry out the operations described herein for temporally synchronizing cine loops of MRI images, displaying temporally synchronized cine loops of MRI images of cardiac wall motion and/or cardiac wall perfusion images and/or evaluation of temporally synchronized cine loops of MRI images. The data portion 356 of memory 236, as shown in the embodiments of FIG. 3, may include MRI image data 362 that includes cine loops of MRI images of wall motion and perfusion.

While the present invention is illustrated, for example, with reference to the cine-loop processing application 360 being an application program in FIG. 3, as will be appreciated by those of skill in the art, other configurations may also be utilized while still benefiting from the teachings of the present invention. For example, the cine-loop processing application 360 may also be incorporated into the operating system 352, the I/O device drivers 358 or other such logical division of the data processing system 230. Thus, the present invention should not be construed as limited to the configuration of FIG. 3 but is intended to encompass any configuration capable of carrying out the operations described herein.

Figure 4:
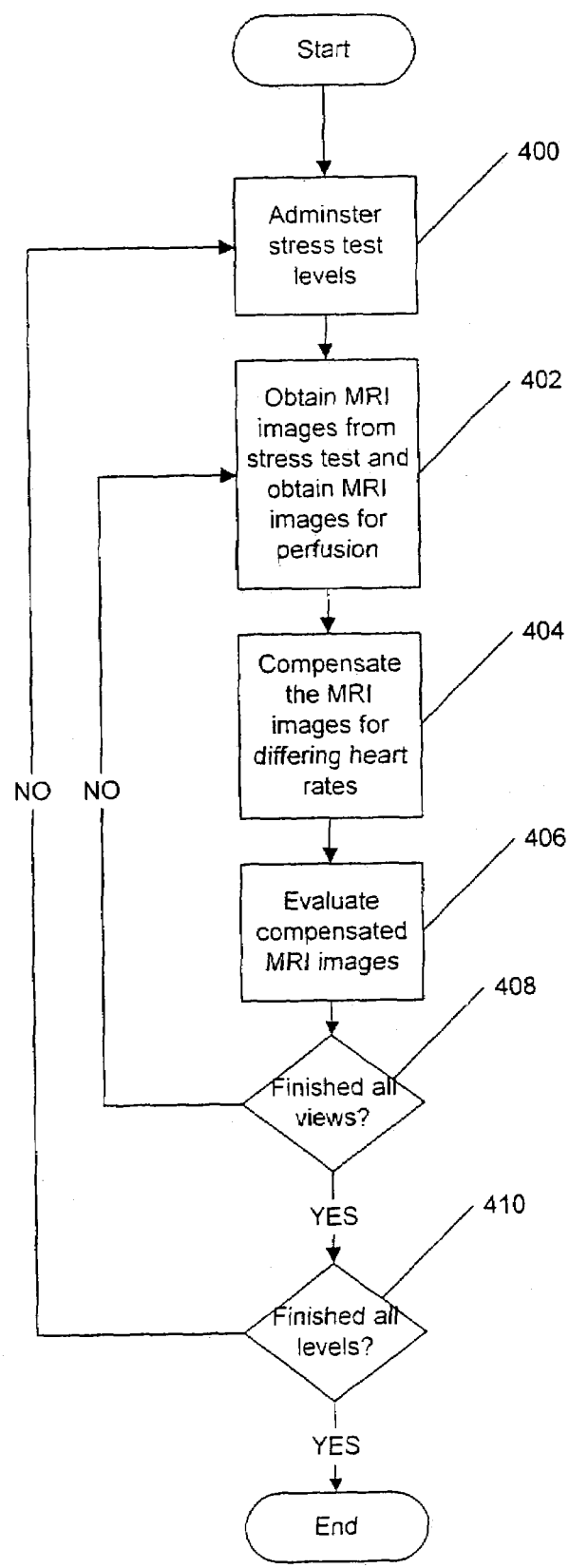
FIG. 4 is a flowchart illustrating operations according to embodiments of the present invention.

FIG. 4 illustrates operations according to certain embodiments of the present invention. As illustrated in FIG. 4, a stress test is administered to a patient (block 400) and MRI images of the heart of the patient indicating wall motion and perfusion are acquired during the stress test (block 402). The stress test may be any type of stress test that may be administered while MRI images are acquired. In particular embodiments the MRI stress test is a biochemically induced stress test using an agent such as dobutamine or the like. The administration of cardiac stress tests are known to those of skill in the art and, therefore, are not described further herein.

The acquired perfusion images may be "first-pass" perfusion images that are acquired shortly after a contrast agent is administered. In such a case, the perfusion images may be a cine loop of images such that the perfusion of the contrast agent may be tracked or monitored by the cine loop images. The perfusion cine loop images. may be multiple perfusion cine loop images for different locations of the heart. These cine loops may be registered to the wall motion cine loop images such that perfusion cine loops correspond to substantially the same locations as the wall motion cine loops. For example, the perfusion cine loops may be three cine loops corresponding to the three short axis wall motion cine loops. Thus, the perfusion images may be acquired at the same planes through the heart as the short axis wall motion images.

Alternatively, or in addition to the generation of a cine loop of perfusion images, myocardial delayed enhancement (MDE) may also be provided. In MDE, 20 minutes after a contrast agent, such as gadolinium DPTA, is administered, some of it has leaked into necrotic (dead) tissue and will appear bright (hence, delayed enhancement). These images may be acquired not as cine loops, but as single images, registered (at the same slice locations) with the corresponding perfusion and/or wall motion images. MDE is another form of perfusion, that is, it is perfusion of dead tissue, while first-pass perfusion is perfusion of living tissue. Thus, the perfusion images may include single images, such as MDE images, and/or cine loops of images. One or both may be displayed with the wall motion images.

The MRI images of wall motion, which may provide cine loops of heart beats at differing locations of the heart and/or different dose levels of a stress inducing agent, are temporally synchronized and the number of perfusion images is established such that each cine loop has the same number of MRI images or frames so that each cine loop maybe displayed for the same duration (block 404). Thus, for example, the perfusion cine loops may be synchronized to the wall motion cine loops by having them play cyclically at the same rate as the wall motion images. The synchronization of perfusion cine loops may also be accomplished by adding frames, dropping frames or adjusting the duration of display of frames as described herein. The cine loops of wall motion may also be synchronized to the cardiac cycle such that each cine loop begins at the same portion of the cardiac cycle.

The compensated cine loops of wall motion and the perfusion images and/or cine loops of perfusion images may be provided, for example, to a workstation for display, and may both be evaluated to assess a state of cardiac physiology of the patient (block 406). Such an assessment may be made, for example, by displaying the wall motion and perfusion cine loops for a given location for several or all doses and/or displaying the cine loops for several or all locations for a given dose. By displaying the images as they are acquired near real time evaluation may be performed. Additionally or alternatively, an MDE image or images may also be displayed with the wall motion cine loops. The displayed cine loops and/or image(s) may be evaluated by a physician to assess cardiac physiology. Such an assessment may include, for example, a determination of the presence or absence of CAD, a change in the severity of CAD, the efficacy of a cardiac treatment regime or the like. For example, the perfusion images may be compared to the wall motion images to determine if an area of reduced perfusion corresponds to an area with defective wall motion, thus, providing further confirmation that an occlusion may exist.

These operations may be repeated until the MRI images for the desired locations (block 408) and for the desired stress test levels (block 410) are obtained and compensated as described herein. Thus, if additional views are to be acquired (block 408) operations continue with obtaining additional MRI images (block 402). If additional stress levels are to be evaluated (block 410), operations continue with the administration of additional stress tests (block 400).

The temporal synchronization of the cine loops has been found to allow physicians to evaluate cardiac physiology more effectively without introducing significant artifacts and/or distortions through the temporal synchronization process that would obscure information or provide false information that would lead to invalid evaluations. Furthermore, the temporal synchronization of the cine loops has been found to increase the effectiveness of the evaluation of MRI cine loops as it allows the physician to simultaneously visually compare heart motion at different heart rates where the display heart motion is synchronized to the same portion within the cardiac cycle. Thus, each displayed image is at approximately the same percent of time within a heart beat. Accordingly, differences in wall motion at different heart rates may be directly compared to detect any abnormality. As discussed above, it has been found that the temporal synchronization process described herein allows for such a display without introducing inaccuracies, artifacts or other such distortions that would hinder the evaluation process. Furthermore, the evaluation process may be performed in a sufficiently real-time manner so as to allow a physician to utilize the MRI cine loops to monitor a stress test while the stress test is being performed. Such monitoring may be useful both in administering the stress test and in evaluation of a patient's condition based on the results of the stress test. By providing the cine loop information in a form that allows for simultaneous direct comparison of data for differing heart rates a physician may rapidly assess the cardiac physiology of a patient so as to adjust parameters of the test and/or avoid injury to the patient.

In several conditions, for example, the presence of resting wall motion abnormalities throughout the course of the stress test, or the presence of concentric left ventricular hypertrophy, assessment of wall motion is not adequate for identifying ischemia. For this reason, the combined assessment of myocardial perfusion and/or delayed enhancement and cine wall motion may enhance a reader's ability to identify areas of myocardial necrosis or ischemia not evident with assessments of wall motion alone.

In still further embodiments of the present invention, the evaluation of the cine loops may be performed automatically or partially automatically utilizing image processing techniques. Such an automatic evaluation may be facilitated by the temporal synchronization of the cine loops as data sets having a common size would be provided and corresponding frames within the data sets would correspond to a common portion within a cardiac cycle. For example, the cine loops or a portion of the images within the cine loops may be compared to each other or a reference so as to highlight deviations from a baseline cine loop. Thus, for example, a baseline wall motion cine loop may be compared to differing dose cine loops and the differences displayed and/or compared to thresholds so as to provide an indication and/or assessment of cardiac physiology. These differences could also be compared with a perfusion cine loop or loops of the same region and areas of low perfusion compared to areas of abnormal wall motion. Such a comparison of the cine loops may be made possible and/or simplified because the location within each cine loop corresponds to approximately the same time within the cardiac cycle such that similarly situated frames within differing cine loops may be directly compared to each other.

An automatic comparison may, for example, also include registration of the differing cine loops to the baseline loops. Such a registration may be provided utilizing conventional pattern recognition and/or alignment techniques such that corresponding pixels of the cine loops or portions of the cine loops are each associated with approximately the same physical location within the patient. In particular embodiments, the comparisons may be 3 (x,y,t), 4 (x,y,z,t) and/or 5 (x,y,z,t,dose) dimensional.

The cine loops may be compensated by repeating images, increasing or decreasing the time an image is displayed and/or by removing images from the cine loops. The cine loops may be temporally synchronized by providing the same number of images or frames in each loop. Thus, each displayed heartbeat of the patient may be displayed for the same period of time irrespective of the heart rate at which the cine loop was acquired. Loops which have more frames may have frames removed and loops with fewer frames may have frames added. Frames may be added by repeating frames in the loop. Frames may be added in a virtual manner by increasing the duration that a frame is displayed. Such a virtual addition of frame may need less storage requirement than the physical repetition of frames in a loop. The frames added or removed may be distributed throughout the loop and are preferably distributed substantially evenly throughout the loop. Furthermore, the cine loops may be synchronized to the patients cardiac cycle such that each cine loop begins at approximately the same part in the cardiac cycle. Techniques for synchronizing MRI cine loops to the cardiac cycle of a patient are known to those of skill in the art and, therefore, need not be described further herein.

In particular embodiments of the present invention the display of cine loops is provided in real time. In other embodiments, the display of cine loops is provided in near real time. Such real time or near real time display of cine loops of a patient undergoing stress testing may be utilized to provide safe stress testing by allowing for rapid analysis and monitoring of the stress test such that patient injury may be avoided. In still other embodiments, the display of cine loops is provided from stored information and may be performed "off-line." Such off-line analysis may be suitable for detailed or more time consuming analysis of the cine loops. Furthermore, the acquisition of data, construction of images and/or the transfer of images of a cine loop may be overlapped with each other so as to reduce apparent latency between the acquisition and the display of images.

Figure 5:
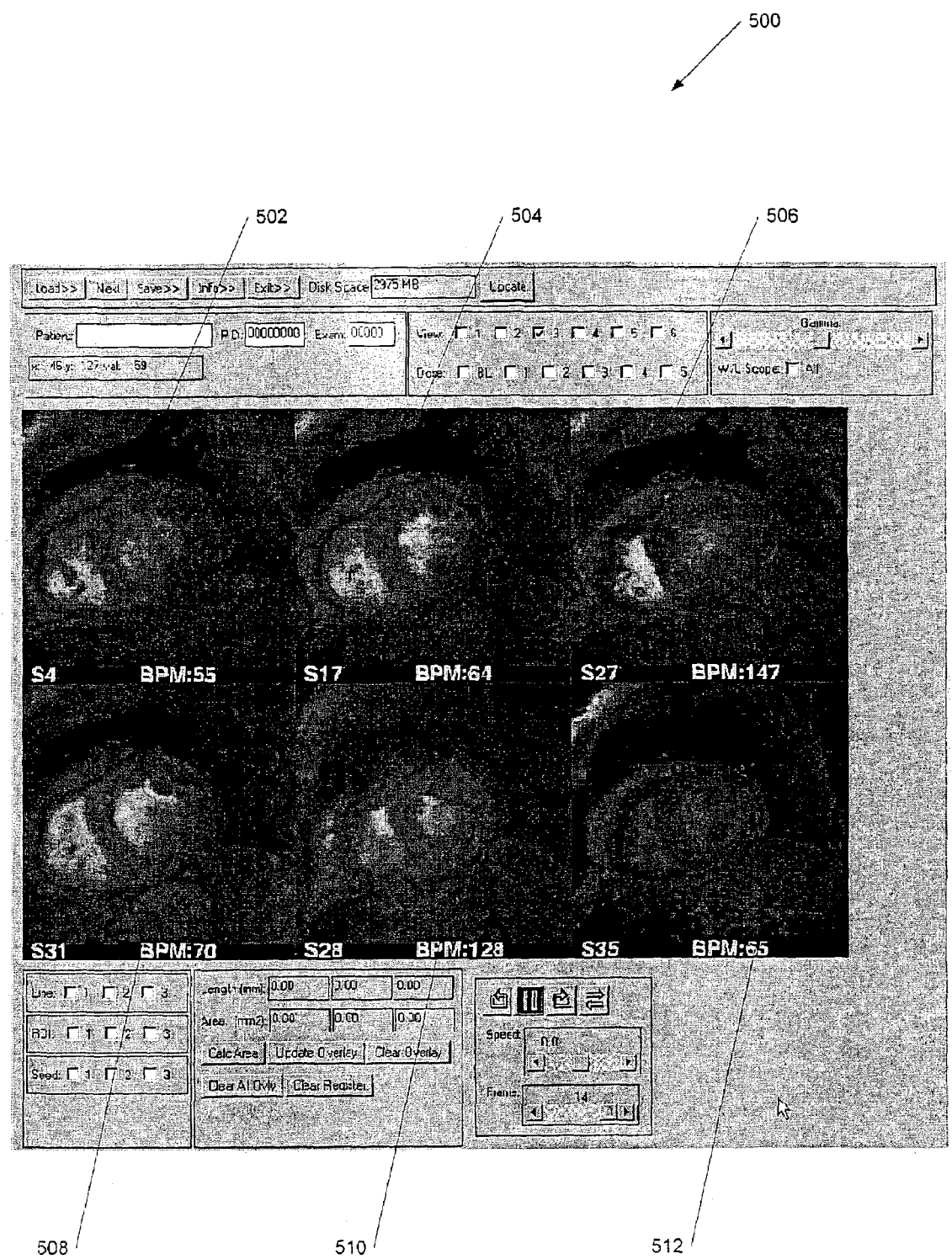
FIG. 5 is a screen capture of an exemplary cine-loop display.

FIG. 5 is a screen capture of a cine loop display 500 according to embodiments of the present invention. As seen in FIG. 5, a plurality of cine loops 502 are simultaneously displayed. The cine loops have been time synchronized as described above and include displays of wall motion and perfusion information. As is seen in FIG. 5, wall motion cine loops, first-pass perfusion cine loops and MDE images may all be displayed simultaneously. In FIG. 5, a baseline wall motion cine loop 502, a first dose wall motion cine loop 504, a peak dose wall motion cine loop 506, a recovery wall motion cine loop 508, a first-pass perfusion cine loop 510 and a delayed enhancement image 512 are simultaneously displayed as described herein.

Figure 6:
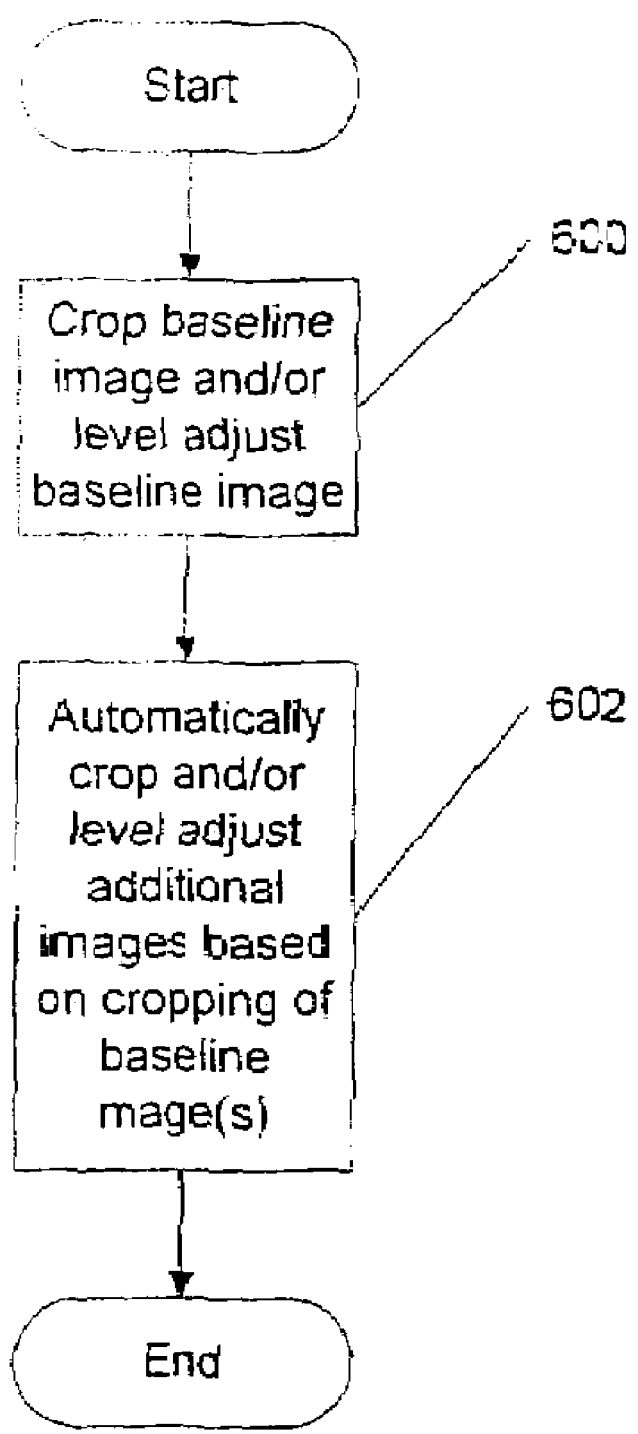
FIG. 6 is a flowchart illustrating operations according to further embodiments of the present invention.

FIG. 6 illustrates operations according to further embodiments of the present invention. As seen in FIG. 6, user input may be obtained to crop a cine loop base image and/or to adjust contrast, brightness, gamma or other display levels of the base cine loop image (block 600). The cropping and/or level adjustment may then be propagated automatically to the remaining images in the base cine loop and to the other cine loops that are displayed or are stored (block 604). Thus, a physician may rapidly adjust the display of the cine loop images without the need to adjust each image and/or loop individually. Optionally, the cropping and/or level information may be stored and associated with the cine loops. The cine loops may also be stored, for example, on a hard drive or other storage media, and recalled at a later time for display and/or analysis. The stored cine loops could then be displayed with the cropping and/or level information automatically applied.

While embodiments of the present invention have been described primarily with reference to near real time evaluation of the MRI images, as will be appreciated by those of skill in the art in light of the present disclosure, evaluation of the MRI images could also occur "off line" or after a substantial delay. For example, prior MRI images could be displayed and compared with current MRI images to determine if improvement, possibly resulting from a course of treatment, has occurred in wall motion and/or perfusion. Thus, the present invention should not be construed as limited to the evaluation of MRI cine loop images immediately after acquisition.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims.

That which is claimed is:

1. A method of displaying cardiac information of a patient having a cardiac cycle, comprising:
   obtaining a plurality of MRI cine loops of the heart of the patient at a plurality of heart rates, the plurality of cine loops including cine loops including frames of wall motion images at different heart beat rates and at least one cine loop including frames of perfusion images of at least one cardiac location;
   synchronizing images in the wall motion cine loops so that heart motion at the different heart beat rates correspond to the same portion of the cardiac cycle and adjusting the at least one perfusion cine loop to have the same number of frames as the wall motion cine loops; and
   simultaneously displaying both wall motion cine loops and the at least one perfusion cine loop.

2. The method of claim 1, further comprising adjusting a number of frames in ones of the displayed wall motion cine loops and/or the perfusion cine loop so that the displayed wall motion cine loops and the perfusion cine loop have the same number of frames, wherein each displayed corresponding image of wall motion in the cine loops is displayed at approximately the same percent of time within a heart beat.

3. The method of claim 1, wherein obtaining a plurality of MRI cine loops comprises acquiring a plurality of MRI cine loops while a stress test is administered to the patient.

4. The method of claim 1, further comprising evaluating the displayed MRI cine loops to determine a presence or absence of coronary artery disease based on the displayed cine loops.

5. A method of displaying cardiac information of a patient, comprising:
   obtaining a plurality of MRI cine loops of the heart of the patient at a plurality of heart rates, the plurality of cine loops including cine loops including frames of wall motion images and at least one cine loop including frames of perfusion images of at least one cardiac location;
   synchronizing the MRI wall motion cine loops to concurrently display images corresponding to the same portion of a cardiac cycle of the patient; and
   simultaneously displaying both the wall motion cine loops and the at least one perfusion cine loop,
   wherein simultaneously displaying comprises simultaneously displaying a plurality of cine loops for differing locations associated with the heart of the patient for a single dosage of a stress inducing agent.

6. A method of displaying cardiac information of a patient, comprising:
   obtaining a plurality of MRI cine loops of the heart of the patient at a plurality of heart rates, the plurality of cine loops including cine loops including frames of wall motion images and at least one cine loop including frames of perfusion images of at least one cardiac location;
   synchronizing the MRI cine loops to concurrently display images corresponding to the same portion of a cardiac cycle of the patient; and
   simultaneously displaying both wall motion cine loops and the at least one perfusion cine loop,
   wherein simultaneously displaying comprises simultaneously displaying a plurality of cine loops for a single location associated with the heart of the patient for differing dosages of a stress inducing agent.

7. The method of claim 2, wherein adjusting comprises adding frames to and/or removing frames from at least one of the displayed wall motion cine loops or the perfusion cine loop.

8. The method of claim 7, wherein adding frames comprises repeating frames of an MRI cine loop.

9. The method of claim 7, wherein the frames that are added to or removed from one of the displayed cine loops such that the added or removed frames are substantially evenly distributed throughout the one of the displayed cine loops.

10. The method of claim 1, wherein the MRI cine loops that are simultaneously displayed include a baseline cine loop of wall motion, a first-dose wall motion cine loop, a peak dose wall motion cine loop, a recovery wall motion cine loop, and a first pass perfusion cine loop, wherein the wall motion MRI cine loops are synchronized such that corresponding frames in each of the plurality of wall motion MRI cine loops correspond to a common portion within the cardiac cycle of the patient, and wherein the perfusion cine loop is synchronized to the wall motion cine loops.

11. The method of claim 2, wherein adjusting the plurality of MRI cine loops comprises adjusting a duration of display of frames of a least one of the plurality of MRI cine loops such that each of the MRI cine loops has a common total duration.

12. The method of claim 11, wherein frames for which the duration is adjusted are evenly distributed throughout the adjusted MRI cine loop.

13. A system for displaying cardiac information of a patient, comprising:
   means for obtaining a plurality of MRI cine loops of the heart of the patient at a plurality of heart rates, the plurality of cine loops including cine loops including frames of wall motion images and at least one cine loop including frames of perfusion images of at least one cardiac location;
   means for synchronizing the plurality of cine loops of MRI images of cardiac wall motion so that heart motion at the different heart beat rates is synchronized to the same portion of the cardiac cycle;
   means for registering the plurality of wall motion cine loops to the at least one cardiac perfusion cine loop; and
   means for simultaneously displaying both wall motion cine loops and the at least one perfusion cine loop.

14. A computer program product for displaying cardiac information of a patient, comprising:
   a computer readable medium having computer readable program code embodied therein, the computer readable program code comprising:
   computer readable program code configured to obtain a plurality of MRI cine loops of the heart of the patient at a plurality of heart rates, the plurality of cine loops including cine loops including frames of wall motion images and at least one cine loop including frames of perfusion images of at least one cardiac location;
   computer readable program code configured to synchronize the plurality of cine loops of MRI images of cardiac wall motion so that heart motion at the different heart beat rates is synchronized to the same portion of the cardiac cycle; and
   computer readable program code configured to simultaneously display both wall motion cine loops and the at least one perfusion cine loop.

15. A method of displaying cardiac information of a patient, comprising:
   obtaining a plurality of MRI cine loops of the heart of the patient at a plurality of heart rates, the plurality of cine loops including cine loops including frames of wall motion images;
   obtaining at least one MRI perfusion image of at least one cardiac location;
   obtaining at least one MRI delayed enhancement image; and
   simultaneously displaying the wall motion cine loops, the at least one perfusion image, and the at least one delayed enhancement image.

16. The method of claim 15, wherein the at least one perfusion image comprises a plurality of perfusion images to provide a cine loop of perfusion images and wherein simultaneously displaying both wall motion cine loops and the at least one perfusion image comprises simultaneously displaying both wall motion cine loops and the at least one cine loop of perfusion images as well as the at least one delayed enhancement image.

17. The method of claim 15, wherein the at least one perfusion image comprises a myocardial delayed enhancement perfusion image.

18. The method of claim 1, wherein the displaying is carried out while a patient is in an MRI scanner to allow a clinician to monitor a patient during a stress test.

19. The method of claim 1, wherein the displaying is carried out so that the cine loops are displayed in real time or near-real time thereby allowing a clinician to monitor cardiac status of a patient undergoing a stress test.

20. A system according to claim 13, wherein the means for acquiring and displaying are carried out so that the cine loops are displayed in real time or near-real time thereby allowing a clinician to monitor cardiac status of a patient undergoing a stress test.

21. A computer program product according to claim 14, wherein the computer readable program code is configured to simultaneously display the cine loops in real time or near real time.

22. A method according to claim 15, wherein the simultaneously displaying step is carried out in real time or near real time from the obtaining steps.

23. A method of providing cardiac diagnostic data to a clinician during a patient stress test, comprising:
   electronically obtaining a plurality of MRI cardiac images of the patient and generating a plurality of wall motion cine loops including: (a) a first baseline wall motion cine loop, (b) a second wall motion cine loop obtained after administration of a contrast agent, and (c) a third recovery wall motion cine loop obtained after the first and second cine loops;
   electronically obtaining MRI perfusion cardiac images of the patient and generating at least one MRI perfusion cine loop;
   electronically adjusting a frame rate of the at least one MRI perfusion cine loop to display at substantially the same rate as the wall motion cine loops;
   electronically obtaining at least one delayed enhancement MRI image of necrotic cardiac tissue of the patient;
   electronically co-registering the wall motion and at least one perfusion cine loops so that the images of the respective cine loops correspond to substantially the same cardiac location of the patient; and
   electronically concurrently displaying the wall motion cine loops, the at least one perfusion cine loop and the at least one delayed enhancement image during a stress test.

24. A system for providing cardiac diagnostic data to a clinician during a patient stress test, comprising:
   means for electronically obtaining a plurality of MRI cardiac images of the patient and generating a plurality of wall motion cine loops including: (a) a first baseline wall motion cine loop, (b) a second wall motion cine loop obtained after administration of a contrast agent, and (c) a third recovery wall motion cine loop obtained after the first and second cine loops;
   means for electronically obtaining MRI perfusion cardiac images of the patient and generating at least one MRI perfusion cine loop;
   means for electronically adjusting a frame rate of the at least one MRI perfusion cine loop to display at substantially the same rate as the wall motion cine loops;

means for electronically obtaining at least one delayed enhancement MRI image of necrotic cardiac tissue of the patient;
means for electronically co-registering the wall motion cine loops and the at least one perfusion cine loop so that the images of the respective cine loops correspond to substantially the same cardiac location of the patient; and
means for electronically concurrently displaying the wall motion cine loops, the at least one perfusion cine loop and the at least one delayed enhancement image during a cardiac stress test in substantially real-time.

25. A method for cardiac diagnostic data to a clinician, comprising:
electronically generating (a) a first baseline wall motion cine loop of MRI cardiac images of the patient, (b) a second wall motion cine loop of MRI cardiac images of the patient obtained after administration of a contrast agent, and (c) a third recovery wall motion cine loop of MRI cardiac images of the patient obtained after the first and second cine loops;
electronically obtaining MRI perfusion cardiac images of the patient and generating at least one MRI perfusion cine loop;
electronically temporally synchronizing the at least one MRI perfusion cine loop to display at substantially the same rate as the wall motion cine loops;
electronically concurrently displaying co-registered wall motion cine loops and the perfusion cine loop in respective multiple display windows of a display during a cardiac stress test in substantially real-time while a patient is undergoing a cardiac stress test in an MRI scanner; and
accepting user input to rapidly adjust at least one of contrast, brightness, gamma or another display level of the baseline cine loop image which is automatically propagated to the other cine loops of the different window displays without adjusting each one separately to thereby provide a clinician with patent information for safer administration of the cardiac stress test.

* * * * *